(12) United States Patent
Pinori et al.

(10) Patent No.: US 7,235,689 B2
(45) Date of Patent: Jun. 26, 2007

(54) HYDROXAMIC ACID DERIVATIVES HAVING ANTI-INFLAMMATORY ACTION

(75) Inventors: Massimo Pinori, Paderno d'Adda (IT); Paolo Mascagni, Villasanta (IT); Rocco Mazzaferro, Milan (IT); Barbara Vergani, Macherio (IT)

(73) Assignee: Italfarmaco SpA, Milan (IT)

( * ) Notice: Subject to any disclaimer, the term of this patent is extended or adjusted under 35 U.S.C. 154(b) by 0 days.

(21) Appl. No.: 10/541,795

(22) PCT Filed: Jan. 7, 2004

(86) PCT No.: PCT/IT2004/000002

§ 371 (c)(1),
(2), (4) Date: Sep. 15, 2005

(87) PCT Pub. No.: WO2004/063146

PCT Pub. Date: Jul. 29, 2004

(65) Prior Publication Data

US 2006/0100285 A1    May 11, 2006

(30) Foreign Application Priority Data

Jan. 10, 2003 (IT) .......................... MI2003A0025

(51) Int. Cl.
*C07C 259/08* (2006.01)
*A61K 31/19* (2006.01)
*A61K 31/47* (2006.01)

(52) U.S. Cl. ........................ 562/621; 514/307; 514/575

(58) Field of Classification Search ..................... None
See application file for complete search history.

(56) References Cited

U.S. PATENT DOCUMENTS 6,034,096 A * 3/2000 Bertolini et al. ............ 514/307

FOREIGN PATENT DOCUMENTS

| WO | WO 96/15105 | 5/1996 |
|---|---|---|
| WO | WO 97/43251 | 11/1997 |
| WO | WO 02/055017 A2 | 7/2002 |
| WO | WO 03/013493 A1 | 2/2003 |

OTHER PUBLICATIONS

Chemical Abstracts Service; Fujii, Setsuro et al; "trans-4-Aminomethylcyclohexane hydroxamic acid"; Database Accession No. 87:39013; Pharmaceutical Co. Ltd., Japan; (2 pgs) XP-002278214, 1977.

Uesato, S., et al; "Novel Histone Deacetylase Inhibitors: N-Hydroxycarboxamides Possessing a Terminal Bicyclic Aryl Group"; *Bioorganic & Medicinal Chemistry Letters*; vol. 12; pp. 1347-1394 (2002).XP-002276408.

Richon, V.M., et al; "A class of hybrid polar inducers of transformed cell differentiation inhibits histone deacetylases"; *Proc. Natl. Acad. Sci.*; vol. 95; pp. 3003-3007 (1998) XP-001120542.

Bouchain, G., et al; "Development of Potential Antitumor Agents, Synthesis and Biological Evaluation of a New Set of Sulfonamide Derivatives as Histone Deacetylase Inhibitors"; *J. Med. Chem.*; vol. 46; pp. 820-830 (2003) XP-002278212.

Lu, Q., et al; $Zn^{2+}$-Chelating Motif-Tethered Short-Chain Fatty Acids as a Novel Class of Histone Deacetylase Inhibitors; *J. Med. Chem.*; vol. 47, pp. 467-474 (2004) XP-002278213.

* cited by examiner

*Primary Examiner*—Sikarl A. Witherspoon
(74) *Attorney, Agent, or Firm*—Nixon & Vanderhye

(57) ABSTRACT

Compounds of formula (I), inhibit TNFα production and may therefore be useful in the treatment of inflammation, of auto-immune diseases, and of pathological conditions which involve excessive production of that cytokine. The compounds of formula (I) are also inhibitors of the histone deacetylase enzyme and may therefore be useful in tumorous diseases, alone or in association with other anti-tumor active ingredients (I)

$$\begin{array}{c}R\\ \diagdown \\ A\end{array}\!\!\!-\!\!\mathrm{L}\!-\!\mathrm{X}\!-\!\underset{\underset{O}{\|}}{\mathrm{C}}\!-\!\mathrm{NH}\!-\!(CH_2)_m\!-\!\mathrm{B}\!-\!(CH_2)_r\!-\!C(O)\!-\!\underset{\underset{R'}{|}}{\mathrm{N}}\mathrm{OH}.$$

14 Claims, No Drawings

HYDROXAMIC ACID DERIVATIVES HAVING ANTI-INFLAMMATORY ACTION

This application is the U.S. National Phase of International Application PCT/IT2004/000002 filed 7 Jan. 2004, which designated the U.S. PCT/IT2004/000002 claims priority to Italian Application No. MI2003A000025 filed 10 Jan. 2003. The entire content of these applications are incorporated herein by reference.

FIELD OF THE INVENTION

The present invention relates to derivatives of hydroxamic acid, in particular derivatives of N-hydroxy benzamide, with anti-inflammatory and anti-tumour activity.

BACKGROUND OF THE INVENTION

Derivatives of hydroxamic acid with anti-inflammatory and immunosuppressive activity are described in U.S. Pat. No. 6,034,096. These compounds can inhibit the production of pro-inflammatory cytokines, in particular of TNFα (tumour necrosis factor) and of interleukin-1-beta and can therefore be used in the treatment of conditions which involve excessive production of those substances, such as inflammatory and auto-immune diseases or tumorous forms.

The compounds described in U.S. Pat. No. 6,034,096 are characterized in that they contain two cyclic structures which are linked by a carbamate or urea group and one of which is in turn linked to an N,hydroxy-carboxyamide (hydroxamic acid) group.

SUMMARY OF THE INVENTION

It has now been found that, by introducing suitable substituent groups, other than those described in U.S. Pat. No. 6,034,09 6, into the first cyclic structure, it is possible to modulate the potency of the TNFα inhibitory activity and to obtain compounds which are metabolically stable and only slightly cytotoxic.

These compounds can therefore usefully be used for the treatment of inflammatory and/or auto-immune diseases in which the production of TNFα and of other pro-inflammatory cytokines performs a pathological role.

It has also been found that the compounds of the present invention are inhibitors of histone deacetylase (HDAC) enzymes and, as such, can also usefully be used in the treatment of various tumorous, auto-immune or neurodegenerative pathological conditions, for which the inhibition of those enzymes is useful.

DESCRIPTION OF THE INVENTION

The subject of the present invention is derivatives of hydroxamic acid of formula (I):

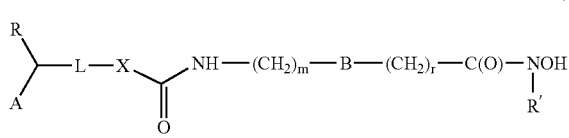

in which
R is hydrogen, $C_{1-4}$ alkyl or phenyl;
R' is hydrogen or $C_{1-4}$ alkyl;

A is aryl or a monocyclic, dicyclic, or tricyclic residue, optionally partly or completely unsaturated, containing one or more heteroatoms selected from the group formed by N, S and O and possibly substituted with haloalkyl, alkylsulphonyl, (cycloalkyl)alkyl, alkanoyl, carbonyloxy, alkoxy, thioalkoxy, thiophenoxy, nitro, cyano, oxo, perfluoroalkoxy, perfluoroalkyl, phenyl, phenoxy, phenylalkoxy, benzoyloxy, phenylalkyl, benzoyl, phenylsulphonyl groups, the phenyl, phenoxy, phenylalkoxy, phenylalkyl, benzoyl and benzoyloxy substituents optionally being substituted in the aromatic ring with alkyl, alkoxy, alkylsulphonyl, amino, cyano, hydroxy, nitro, perfluoroalkoxy, perfluoroalkyl, phenylsulphonyl, thioalkoxy and halogen groups;

L is a chain of from 1 to 5 carbon atoms optionally containing a double bond or an NR' group in which R' is as defined above;

X is an oxygen atom, an NR' group in which R' is as defined above, or is absent;

r and m are, independently, 0, 1 or 2;

B is phenyl or cyclohexyl.

Preferred compounds according to the present invention are those in which:
R is hydrogen or methyl, more preferably hydrogen,
A is phenyl, preferably substituted with one or more groups selected from: alkoxy, nitro, perfluoroalkyl, phenoxy, phenyl, phenylalkoxy, benzoyloxy, thioalkoxy;
L is methylene or ethylene and X is absent;
m and r are equal to zero;
B is phenyl;
R' is hydrogen.

Moreover, the following compounds are particularly preferred:

N-hydroxy-4-[2-(4-trifluoromethyl-phenyl)-acetylamino]-benzamide;
N-hydroxy-4-(3-phenyl-butyrylamino)-benzamide;
N-hydroxy-4-[3-(3-methoxy-phenyl)-propionylamino]-benzamide;
N-hydroxy-4-[2-(4-methoxy-phenyl)-acetylamino]-benzamide;
N-hydroxy-4-[2-(4-ethoxy-phenyl)-acetylamino]-benzamide;
N-hydroxy-4-[3-(3,5-bis-trifluoromethyl-phenyl)-propionylamino]-benzamide;
N-hydroxy-4-[2-(3,4,5-trimethoxy-phenyl)-acetylamino]-benzamide;
N-hydroxy-4-[2-(4-methylsulphanil-phenyl)-acetylamino]-benzamide;
N-hydroxy-4-[2-(3-trifluoromethyl-phenyl)-acetylamino]-benzamide;
N-hydroxy-4-[2-(3-nitro-phenyl)-acetylamino]-benzamide;
N-hydroxy-4-[2-(3-phenoxy-phenyl)-acetylamino)-benzamide;
N-hydroxy-4-[2-(diphenyl-4-yl)-acetylamino]-benzamide;
N-hydroxy-4-[2-(2,3-dimethoxy-phenyl)-acetylamino]-benzamide;
2-[2-(4-hydroxycarbamoyl-phenylcarbamoyl)-ethyl]-phenyl ester of benzoic acid;
N-hydroxy-4-[2-(4-nitro-phenyl)-acetylamino]-benzamide;
N-hydroxy-4-[2-(2-phenoxy-phenyl)-acetylamino]-benzamide;
N-hydroxy-4-[2-(4,5-dimethoxy-2-nitro-phenyl)-acetylamino]-benzamide;
N-hydroxy-4-[2-(2-benzyloxy-phenyl)-acetylamino]-benzamide;

N-hydroxy-4-[2-(2-nitro-phenyl)-acetylamino]-benzamide.

Compounds of general formula (I), and this is a first aspect of the invention, can inhibit in vitro and in vivo, at nanomolar concentrations, the production of TNFα and of other pro-inflammatory cytokines.

A second aspect of the present invention consists of the use of compounds of the general formula (I), alone or in combination with other active ingredients, for the treatment of inflammatory and auto-immune pathological conditions which are characterized by excessive production of TNFα and/or of other pro-inflammatory cytokines such as, for example, spondyloarthropathy (*Expert Opin. Emerging Drugs* (2002) 7(2):235–246), rheumatoid arthritis (*Lancet* (1999) 354(9194): 1932), acute alcoholic hepatitis (*Am. J. Gastroenterology* (2001) 96(12):3361–3367), inflammatory syndromes of the intestine such as Crohn's disease and ulcerative colitis (*Drugs of Today* (2000) 36(5):281–293), heart failure (*Heart Fail. Rev.* (2001) 6(2): 143), asthma (*Int. J. Biochem. Cell Biol.* (2000) 32(8): 833), intracerebral haemorrhage (*Stroke* (2001) 32:240–248), psoriasis (*Drugs Today* (1999) 35(12):913), diabetes (*J. Autoimmun.* (2003) 20(4):303–312-*Pancreas.* (2003) 26(4):E99–E104), etc.

In a third aspect of the invention, the compounds of general formula (I) are inhibitors of the activity of the histone deacetylase enzymes.

A further aspect of the invention therefore consists of the use of compounds of general formula (I), alone or in combination with other active ingredients, for the treatment of tumorous pathological conditions (TRENDS in *Endocrinology & Metabolism* (2001) 12 (7):294–300), neurodegenerative pathological conditions (*Nature* (2001) 413:739–743), and auto-immune pathological conditions (*J. Clinical Investigation* (2003) 111:539–552).

The compounds (I) are also inhibitors of the histone deacetylase enzyme and may therefore be useful in tumorous diseases, alone or in combination with other anti-tumour active ingredients; to maximize the anti-tumour effect, the compounds (I) are preferably administered in combination with anti-tumour active ingredients having an action mechanism other than HDAC inhibition, such as, for example, anti-proliferative active ingredients.

Pharmaceutical compositions which contain compounds of formula (I) are therefore also subjects of the present invention; these compositions may be in the form of capsules, tablets, coated tablets, creams, ointments or phials for oral, intramuscular, or intravenous administration.

In the above-mentioned pharmaceutical compositions, the compounds of formula (I), alone or in combination with other active ingredients, may optionally be mixed with conventional excipients or vehicles, for example, those described in Remington's Pharmaceutical Sciences Handbook, XVII, ed. Mack Pub., N.Y., U.S.A.

The compounds of formula (I) may be prepared by the method described in U.S. Pat. No. 6,034,096, which is incorporated herein by reference. Alternatively, the compounds of the invention may be prepared by "solid phase" organic synthesis with the use of one of the commercially available special resins for N-hydroxyamides. For example, a polystyrene resin cross-linked with divinyl benzene, functionalized with O-alkylated hydroxylamine groups from para-alkoxybenzyl residues (Wang type resins) may be used [see e.g. Richter, L. S. and Desai M. C., *Tetrahedron Letters* (1996) 38(3): 321–322].

The amine groups that are present in the resin may by acylated by suitably protected amino-acids in the presence of suitable condensing agents to give intermediates of formula $$G-NH-(CH_2)_m-B-(CH_2)_r-CONHO-Resin \quad (II)$$

where G is a suitable protector group and m, r and B have the meanings defined for the general formula (I).

After removal of the protector group G, the amine group can be further acylated with the use, after activation or in the presence of suitable condensing agents, of acids of formula (III):

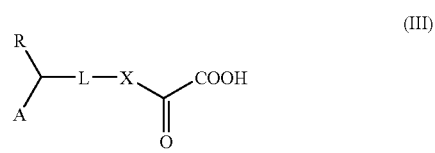

where R, A, L and X have the meanings defined for the general formula (I).

Finally, the products of the invention can be released from the resin by treatment with medium strength acids (for example, trifluoroacetic acid), filtration and possibly final purification.

The present invention will be illustrated below by means of some examples which have the purpose purely of further describing the subjects of the present invention and are not intended as in any way limiting thereof.

EXAMPLES

The following abbreviations are used in the examples given below:
ACN acetonitrile
PVDF polyvinylidene difluoride
DCM dichloromethane
DMF dimethyl formamide
HOAt 1-hydroxy-7-azabenzotriazole
HATU O-(7-azabenzotriazol-1-yl)-N,N,N'N'-tetramethyluronium hexafluorophosphate
TFA trifluoroacetic acid General Purification Method Unless indicated otherwise, all of the final purifications were performed by a Waters HPLC/MS preparation system with a Waters Symmetry C18 5 μm 19×50 mm column equipped with a Waters ZQ mass spectrometer;

Operative Conditions:

ES+ centroid ionization, scanning time 15 min., scanning m/z 120–1000, cone voltage 15V, source temperature 120° C., salvation temperature 250° C.

HPLC Eluents:
A=$H_2O$, B=ACN, C=HCOOH 1% in $H_2O$

Gradient:

| Time (min) | A | B | C | Flow (ml/min) |
|---|---|---|---|---|
| 0 | 94% | 5% | 1% | 20 |
| 2 | 94% | 5% | 1% | 20 |
| 3 | 87% | 12% | 1% | 20 |
| 8 | 87% | 12% | 1% | 20 |
| 11 | 20% | 80% | 1% | 20 |
| 12 | 94% | 5% | 1% | 20 |

An aliquot of the crude product to be purified (30–50 mg) was dissolved in 0.1 ml of MeOH and diluted with 0.4 ml of ACN/H$_2$O mixture (1:1; v/v). The solution was filtered on 0.45 μm PVDF membrane and was injected into the preparation system described above. For each run, the fractions corresponding to the peak associated with the expected molecular ion ([M+H]$^+$) were collected, recombined and concentrated to dryness.

Example 1

N-hydroxy-4-[2-(4-trifluoromethyl-phenyl)-acetylamino]-benzamide

Step A

A mixture of HOAt (55 mg, 0.4 mmoles) and HATU (152 mg, 0.4 mmoles) in anhydrous DMF (6.5 ml), followed by diisopropyl ethylamine (0.14 ml, 0.8 mmoles), was added to a solution of 4-(9H-fluoren-9-yl-methoxycarbonylamino)-benzoic acid (150. mg, 0.4 mmoles) in anhydrous DMF (0.5 ml). The reaction mixture was stirred at ambient temperature for 30 minutes and was then transferred into a reactor containing a Wang type polystyrene resin, functionalized with hydroxylamine (0.1 g; 0.1 mmoles), and the suspension was stirred at ambient temperature for 16 hours. The resin was filtered and washed, in sequence, with DMF (5×2 ml), DCM (2×2 ml), MeOH (2×2 ml), DCM (2×2 ml), MeoH (2×2 ml), DCM (2×2 ml) and DMF (5×2 ml); finally, the resin was filtered and dried under vacuum.

Step B

The resin obtained in A was expanded in a 20% solution of piperidine in DMF (1 ml) and stirred at ambient temperature for one hour and was then filtered, washed with DMF (5×2 ml), and dried under vacuum.

Step C

HATU (381 mg, 1 mmole) and diisopropyl ethylamine (262 μl, 1.5 mmoles) were added to a solution of (4-trifluoromethyl-phenyl)-acetic acid (184 mg, 0.9 mmoles) in anhydrous DMF (1 ml). The reaction mixture was stirred at ambient temperature for 30 minutes and was then added to the resin obtained in B and stirred again at ambient temperature for 20 hours. The resin was filtered and washed, in sequence, with DMF (5×2 ml), DCM (2×2 ml), MeOH (2×2 ml), DCM 2×2 ml), MeoH (2×2 ml), DCM (5×2 ml) and, finally, was filtered and dried under vacuum.

Step D

The resin obtained in C was expanded in a 50% solution of TFA in DCM (1 ml) and was subjected to stirring at ambient temperature for one hour and was then filtered and the solution was evaporated to dryness. The residue was taken up with t-BuOMe and re-evaporated to dryness five times. The crude product thus obtained was purified by preparation HPLC/MS, following the general method described above.

10.5 mg was obtained; [M+H]$^+$=339.3 (calc. 339.1)

Example 2

N-hydroxy-4-(3-phenyl-butyrylamino)-benzamide

The product was prepared by the method described in Example 1, with the use of 3-phenyl-butyric acid in step C.

8.9 mg was obtained; [M+H]$^+$=299.3 (calc. 299.1)

Example 3

N-hydroxy-4-[3-(3-methoxy-phenyl)-propionylamino]-benzamide

The product was prepared by the method described for Example 1, with the use of 3-(3-methoxy-phenyl)-propionic acid in step C.

15.7 mg was obtained; (M+H]$^+$=315.3 (calc. 315.1)

Example 4

N-hydroxy-4-[2-(4-methoxy-phenyl)-acetylamino]-benzamide

Step A 4,methoxy-phenyl acetic acid (5 g) was suspended in chloroform (150 ml); thionyl chloride (10.8 g) was added to the suspension and was heated to reflux, giving a clear solution. After four hours under reflux, the solvent was evaporated under vacuum and the residue was taken up with further chloroform and evaporated again. The residue was dissolved in tetrahydrofuran (100 ml) and p-amino-benzoic acid (4.1 g) dissolved in tetrahydrofuran (100 ml) was added to the solution. The reaction mixture was left at ambient temperature overnight. The reaction mixture was then evaporated under vacuum and the residue was crystallized from 70% ethanol (250 ml). 5.1 g of product was obtained (yield 60%) with HPLC purity greater than 97%.

[M+H]$^+$=286.3 (calc. 286.1)

Step B

The product obtained in the preceding step (5 g) was suspended in chloroform (150 ml); thionyl chloride (6.3 g) was added to the suspension and was heated to reflux giving a clear solution. After four hours under reflux, the solvent was evaporated under vacuum and the residue was taken up with further chloroform and evaporated again. The residue was dissolved in tetrahydrofuran (100 ml) and added to an aqueous hydroxylamine solution (50% w/w; 6.5 ml) in tetrahydrofuran (100 ml). The reaction mixture was left at ambient temperature overnight. The reaction mixture was then evaporated under vacuum and the residue was crystallized from 70% ethanol (100 ml). 4.14 g of product was obtained (yield 78%) with HPLC purity greater than 99%; m.p.=197.6–200° C. (dec.);

[M+H]$^+$=301.3 (calc. 301.1)

Example 5

N-hydroxy-4-[2-(4-ethoxy-phenyl)-acetylamino]-benzamide

The product was prepared by the method described for Example 1, with the use of 2-(4-ethoxy-phenyl)-acetic acid in step C.

14.9 mg was obtained; [M+H]$^+$=315.3 (calc. 315.1)

Example 6

N-hydroxy-4-[3-(3,5-bis-trifluoromethyl-phenyl)-propionyl-amino]-benzamide

The product was prepared by the method described for Example 1, with the use of 3-(3,5-bis-trifluoromethyl-phenyl)-propionic acid in step C.

14.9 mg was obtained; [M+H]$^+$=421.3 (calc. 421.1)

Example 7

N-hydroxy-4-[2-(3,4,5-trimethoxy-phenyl)-acetylamino]-benzamide

The product was prepared by the method described for Example 1, with the use of 2-(3,4,5-trimethoxy-phenyl)-acetic acid in step C.

11.4 mg was obtained; $[M+H]^+$=361.4 (calc. 361.1).

Example 8

N-hydroxy-4-[2-(4-methylsulphanil-phenyl)-acetylamino]-benzamide

The product was prepared by the method described for Example 1, with the use of 2-(4-methylsulphanil-phenyl)-acetic acid in step C.

10.6 mg was obtained; $[M+H]^+$=317.4 (calc. 317.1)

Example 9

N-hydroxy-4-[2-(3-trifluoromethyl-phenyl)-acetylamino]-benzamide

The product was prepared by the method described for Example 1, with the use of 2-(3-trifluoromethyl-phenyl)-acetic acid in step C.

7.9 mg was obtained; $[M+H]^+$=339.3 (calc. 339.1)

Example 10

N-hydroxy-4-[2-(3-nitro-phenyl)-acetylamino]-benzamide

The product was prepared by the method described for Example 1, with the use of 2-(3-nitro-phenyl)-acetic acid in step C.

16.1 mg was obtained; $[M+H]^+$=316.3 (calc. 316.1)

Example 11

N-hydroxy-4-[2-(3-phenoxy-phenyl)-acetylamino]-benzamide

The product was prepared by the method described for Example 1, with the use of 2-(3-phenoxy-phenyl)-acetic acid in step C.

14.3 mg was obtained; $[M+H]^+$=363.4 (calc. 363.1)

Example 12

N-hydroxy-4-[2-(diphenyl-4-yl)-acteylamino]-benzamide

The product was prepared by the method described for Example 1, with the use of 2-(diphenyl-4-yl)-acetic acid in step C.

9.1 mg was obtained; $[M+H]^+$=347.3 (calc. 347.1)

Example 13

N-hydroxy-4-[2-(2,3-dimethoxy-phenyl)-acetylamino]-benzamide

The product was prepared by the method described for Example 1, with the use of 2-(2,3-dimethoxy-phenyl)-acetic acid in step C.

10.8 mg was obtained; $[M+H]^+$=331.3 (calc. 331.1)

Example 14

2-[2-(4-hydroxycarbamoyl-phenylcarbamoyl)-ethyl]-phenyl ester of benzoic acid

The product was prepared by the method described for Example 1, with the use of 2-(2-carboxy-ethyl)-phenyl ester of benzoic acid in step C.

18.1 mg was obtained; $[M+H]^+$=405.4 (calc. 405.1)

Example 15

N-hydroxy-4-[2-(4-nitro-phenyl)-acteylamino]-benzamide

The product was prepared by the method described for Example 1, with the use of 2-(4-nitro-phenyl)-acetic acid in step C.

7.2 mg was obtained; $[M+H]^+$=316.3 (calc. 316.1)

Example 16

N-hydroxy-4-[2-(2-phenoxy-phenyl)-acetylamino]-benzamide

The product was prepared by the method described for Example 1, with the use of 2-(2-phenoxy-phenyl)-acetic acid in step C.

14.2 mg was obtained; $[M+H]^+$=363.4 (calc. 363.1)

Example 17

N-hydroxy-4-[2-(4,5-dimethoxy-2-nitro-phenyl)-acetylamino]-benzamide

The product was prepared by the method described for Example 1, with the use of 2-(4,5-dimethoxy-2-nitro-phenyl)-acetic acid in step C.

8.6 mg was obtained; $[M+H]^+$=376.3 (calc. 376.1)

Example 18

N-hydroxy-4-[2-(2-benzyloxy-phenyl)-acetylamino]-benzamide

The product was prepared by the method described for Example 1, with the use of 2-(2-benzyloxy-phenyl)-acetic acid in step C.

10.1 mg was obtained; $[M+H]^+$=377.4 (calc. 377.1)

Example 19

N-hydroxy-4-[2-(2-nitro-phenyl)-acetylamino]-benzamide

The product was prepared by the method described for Example 1, with the use of 2-(2-nitro-phenyl)-acetic acid in step C.

12.5 mg was obtained; [M+H]$^+$=316.3 (calc. 316.1)

Example 20

Inhibition of TNFα Production—Determination in vitro

The compounds were dissolved in DMSO to a final concentration of 120 mM and were stored at −80° C. The solutions for the test were prepared by diluting the mother solutions in RPMI 1640 with the addition of 1% FCS and 0.01% DMSO and were filtered with 0.2 μm filters.

Mononuclear peripheral blood cells were obtained from "buffy coats" of healthy donors by separation in a Ficoll-Hypaque gradient. The cells were spread in plates with 96 wells at a concentration of about 500,000 cells per well, suspended in RPMI 1640 containing 1% FCS and were incubated at 37° C. in the presence of various concentrations (from $10^{-6}$ to $10^{-11}$ M) of the compounds to be tested.

After 1 hour, LPS was added (to a final concentration of 10 ng/ml; obtained from E. coli 055:B5) and the plates were incubated at 37° C. for a further 24 hours. Upon completion, the supernatant fluids were collected and used for the determination of the TNFα content by ELISA (ELISA Duoset Kit; R&D systems, Minneapolis, Minn., USA).

The concentration of TNFα was calculated with the use of a calibration curve and the IC$_{50}$ values (concentration which inhibits the production of the cytokine by 50%) were calculated from the curve obtained, giving the percentage inhibition values for each individual concentration of the compound under test.

The values obtained for the compounds described in the preceding examples are given in the following table (the values are the average of the results obtained in at least two determinations, performed with cells of different donors).

TABLE 1

Inhibition of TNFα production in human monocytes stimulated with LPS

| Example | IC$_{50}$ (nM) |
|---|---|
| Ex. 01 | 14.5 |
| Ex. 02 | 76.0 |
| Ex. 03 | 26.0 |
| Ex. 04 | 51.5 |
| Ex. 05 | 32.0 |
| Ex. 06 | 17.0 |
| Ex. 07 | 45.0 |
| Ex. 08 | 320.0 |
| Ex. 09 | 70.0 |
| Ex. 10 | 134.0 |
| Ex. 11 | 108.0 |
| Ex. 12 | 227.0 |
| Ex. 13 | 187.0 |
| Ex. 14 | 157.0 |
| Ex. 15 | 27.0 |
| Ex. 16 | 259.0 |
| Ex. 17 | 280.0 |
| Ex. 18 | 391.0 |
| Ex. 19 | 1000.0 |

Example 21

Inhibition of TNFα Production—Determination in vivo

For the compounds of the present invention, the capacity to inhibit TNFα production induced by the administration of LPS was evaluated in mice.

A lethal quantity of LPS (E. coli 055:B5; 2 mg/kg) was administered to the animals (CD1 female mice) by an intraperitoneal route; 90 min. after administration, the animals were killed and the TNFα content present in the blood was determined by ELISA assay.

The compounds under test, suspended in Methyl Cellosolve (0.5% in water), were administered orally, 60 min. prior to the administration of LPS, at a dose of 1 mg/kg.

The results are given in the following table; the values are expressed as percentage inhibition of TNFα production in comparison with the control group.

TABLE 2 inhibition of TNFα production in mice

| Example | Inhibition |
|---|---|
| Ex. 01 | 67% |
| Ex. 03 | 56% |
| Ex. 04 | 42% |

Example 22

Metabolic Resistance in vitro

The metabolic resistance of some compounds described in the preceding examples was evaluated by incubating the substances with the S9 fraction of a microsomal preparation of liver cells. Each compound (6 μg/ml) was incubated at 37° C. for 30 min. in phosphate buffer (pH 7.4) containing the S9 fraction (protein content 2 mg/ml). The reaction was stopped by cooling in an ice bath and adding an equal volume of water/acetonitrile (50:50) containing 0.2% of trifluoroacetic acid. After centrifuging, an aliquot of the supernatant fluid was analyzed by HPLC to evaluate the percentage of product that had remained intact.

The percentages of unchanged product that were present after incubation for 30 min. are given in the following table.

TABLE 3 metabolic transformation by means of the S9 liver fraction

| Examples | Residual product after 30 min. |
|---|---|
| Ex. 01 | 78.9% |
| Ex. 03 | 60.7% |
| Ex. 04 | 90.2% |
| Ex. 05 | 89.0% |
| Ex. 06 | 68.4% |

Example 23

Cytotoxicity in vitro

The cytotoxicity of some compounds described in the preceding examples was evaluated in vitro on the human HEP-G2 hepatoma cell line by a commercial colorimetric method (Cell Titer 96® Aqueous One Solution Cell Proliferation Assay—Promega); the method determines the number of living cells on the basis of their ability to metabolize a tetrazolium salt producing formazane. The quantity of formazane produced is proportional to the number of living cells.

The HPE-G2 cells were distributed in micro-plates with 96 wells at a density of $4 \times 10^4$ cells/well (100 μl) in M199 medium containing 10% of bovine foetal serum and supplements (complete medium).

After incubation for 24 h (37° C., 5% $CO_2$, 90% humidity) the cells were washed once and the medium was replaced with 200 μl of complete medium containing the substances to be tested at final concentrations of $10^{-5}$, $10^{-6}$ and $10^{-7}$ M. The test was performed in triplicate.

The plates were incubated for a further 48 h, after which 100 μl of medium was removed and 20 μl per well of dye solution was added in accordance with the supplier's instructions. The optical density ($\lambda$=490 nm) was read after incubation for 1 h at 37° C. with the use of a plate reader (Victor 2—Wallace Perkin Elmer).

The results are expressed as the percentage inhibition of the formation of formazane in comparison with the control. The values obtained at the concentration of $10^{-6}$ M are given in the following table.

TABLE 4

| percentages of cytotoxicity towards HEP-G2 cells | |
|---|---|
| Example | Cytotoxicity at $10^{-6}$ M |
| Ex. 01 | 3.8% |
| Ex. 03 | 7.3% |
| Ex. 04 | 0% |
| Ex. 05 | 0% |
| Ex. 06 | 13% |
| Ex. 15 | 0% |

Example 24

Inhibition of the Enzymatic Activity of Histone Deacetylase

The capacity of the compounds of the invention to inhibit the activity of the histone deacetylase enzyme was evaluated with the use of the mouse HADC-1 enzyme. The assay was performed by the method already described in the literature [Biochem. Biophys. Acta, 1996, vol. 1296, p. 181]. The $IC_{50}$ values (concentration which inhibits the activity of the enzyme by 50%) were derived from the percentages of inhibition obtained with various concentrations of the compound under test; these values are given in the following table.

TABLE 5

| inhibition of mouse HDAC-1 enzyme | |
|---|---|
| Example | $IC_{50}$ (nM) |
| Ex. 01 | 142.0 |
| Ex. 03 | 219.0 |
| Ex. 04 | 113.0 |
| Ex. 05 | 90.0 |
| Ex. 06 | 19.0 |
| Ex. 07 | 14.0 |
| Ex. 08 | 58.0 |
| Ex. 09 | 67.0 |

TABLE 5-continued

| inhibition of mouse HDAC-1 enzyme | |
|---|---|
| Example | $IC_{50}$ (nM) |
| Ex. 10 | 130.0 |
| Ex. 11 | 102.0 |
| Ex. 12 | 7.0 |
| Ex. 13 | 202.0 |
| Ex. 14 | 106.0 |
| Ex. 15 | 146.0 |
| Ex. 16 | 118.0 |
| Ex. 17 | 255.0 |
| Ex. 18 | 112.0 |
| Ex. 19 | 214.0 |

The invention claimed is:

1. A compound of formula (I):

$$\begin{array}{c} R \\ \diagdown \\ \diagup \\ A \end{array} L-X-\underset{\underset{O}{\|}}{C}-NH-(CH_2)_m-B-(CH_2)_r-C(O)-\underset{\underset{R'}{|}}{N}OH \qquad (I)$$

in which:
R is hydrogen, $C_{1-4}$ alkyl or phenyl;
R' is hydrogen or $C_{1-4}$ alkyl;
A is phenyl substituted with one or more groups selected from: alkoxy, nitro, perfluoroalkyl, phenoxy, phenyl, phenylalkoxy, benzoyloxy, and thioalkoxy;
L is absent;
X is absent;
r and m are, independently, 0, 1 or 2;
B is phenyl.

2. The compound according to claim 1 in which R is hydrogen.

3. The compound according to claim 1 in which R is methyl.

4. The compound according to claim 1 in which A is phenyl substituted with at least one group selected from the group consisting of alkoxy, nitro, perfluoroalkyl, phenoxy, phenyl, phenylalkoxy, benzoyloxy and thioalkoxy.

5. The compound according to claim 1 in which m and r are equal to zero.

6. The compound according to claim 1 in which R' is hydrogen.

7. A compound selected from the group consisting of:
N-hydroxy-4-[2-(4-trifluoromethyl-phenyl)-acetylamino]-benzamide;
N-hydroxy-4-[3-(3-methoxy-phenyl)-propionylamino]-benzamide;
N-hydroxy-4-[2-(4-methoxy-phenyl)-acetylamino]-benzamide;
N-hydroxy-4-[2-(4-ethoxy-phenyl)-acetylamino]-benzamide;
N-hydroxy-4-[3-(3,5-bis-trifluoromethyl-phenyl)-propionylamino]-benzamide;
N-hydroxy-4-[2-(3,4,5-trimethoxy-phenyl)-acetylamino]-benzamide;
N-hydroxy-4-[2-(3-trifluoromethyl-phenyl)-acetylamino]-benzamide;
N-hydroxy-4-[2-(3-nitro-phenyl)-acetylamino]-benzamide;

N-hydroxy-4-[2-(3-phenoxy-phenyl)-acetylamino]-benzamide;
N-hydroxy-4-[2-(diphenyl-4-yl)-acetylamino]-benzamide;
N-hydroxy-4-[2-(2,3-dimethoxy-phenyl)-acetylamino]-benzamide;
2-[2-(4-hydroxycarbamoyl-phenylcarbamoyl)-ethyl]-phenyl ester of benzoic acid;
N-hydroxy-4-[2-(4-nitro-phenyl)-acetylamino]-benzamide;
N-hydroxy-4-[2-(2-phenoxy-phenyl)-acetylamino]-benzamide;
N-hydroxy-4-[2-(4,5-dimethoxy-2-nitro-phenyl)-acetylamino]-benzamide;
N-hydroxy-4-[2-(2-benzyloxy-phenyl)-acetylamino]-benzamide; and
N-hydroxy-4-[2-(2-nitro-phenyl)-acetylamino]-benzamide.

8. The compound according to claim 7 which is N-hydroxy-4-[2-(4-methoxy-phenyl)-acetylamino]-benzamide.

9. Method of treatment of an inflammatory and/or autoimmune condition in a patient in need of such treatment comprising administering to said patient and effective amount of a compound of claim 1.

10. A method for the treatment of tumorous and/or neurodegenerative diseases in a patient in need of such treatment comprising administering to said patient an effective amount of a compound of claim 1.

11. A method for the treatment of tumorous and/or neurodegenerative diseases in a patient in need of such treatment comprising administering to said patient an effective amount of a compound of claim 1 and at least one active ingredient with anti-tumour action.

12. A pharmaceutical composition comprising a compound of claim 1 mixed with suitable excipients and/or vehicles.

13. A pharmaceutical composition comprising a compound of claim 1 and at least one active ingredient with anti-tumour action mixed with suitable excipients and/or vehicles.

14. Method according to claim 9, wherein said condition is selected from the group consisting of spondyloarthropathy, rheumatoid arthritis, acute alcoholic hepatitis, inflammatory syndromes of the intestine (Crohn's disease and ulcerative colitis), asthma, diabetes, heart failure, intracerebral heamorrhage, psoriasis, atopic dermatitis, contact dermatitis, glomerulonephritis, systemic lupus erythematosus, chronic pulmonary obstruction, pulmonary fibrosis, multiple sclerosis, sepsis, and septic shock.

* * * * *